United States Patent [19]

Coussement et al.

[11] Patent Number: 5,659,028
[45] Date of Patent: Aug. 19, 1997

[54] BRANCHED FRUCTO-OLIGOSACCHARIDES, METHOD FOR OBTAINING THEM AND USE OF PRODUCTS CONTAINING THEM

[75] Inventors: Paul Coussement, Pellenberg; Leen De Leenheer, Tervuren; Georges Smits, Gijzegem-Aalst, all of Belgium

[73] Assignee: Raffinerie Tirlemontoise S.A., Belgium

[21] Appl. No.: 375,004

[22] Filed: Jan. 18, 1995

Related U.S. Application Data

[63] Continuation of Ser. No. 920,472, filed as PCT/BE91/00014 Feb. 22, 1991, published as WO91/13076 Sep. 5, 1991, abandoned.

[30] Foreign Application Priority Data

Feb. 23, 1990 [BE] Belgium .................. 9000213

[51] Int. Cl.$^6$ ............... C08B 37/00; C08B 37/18; A61K 31/715
[52] U.S. Cl. .............. 536/123; 426/658; 536/123.1; 536/124
[58] Field of Search ............... 536/123; 435/101; 426/658; 514/54, 824, 892

[56] References Cited

U.S. PATENT DOCUMENTS

| | | | |
|---|---|---|---|
| 4,277,563 | 7/1981 | Kerkhoffs | 435/99 |
| 4,613,377 | 9/1986 | Yamazaki et al. | 127/39 |
| 4,734,402 | 3/1988 | Hashimoto et al. | 514/54 |
| 4,788,065 | 11/1988 | Nakamura et al. | 426/2 |
| 4,859,488 | 8/1989 | Kan et al. | 426/658 |
| 5,122,460 | 6/1992 | Uchiyama et al. | 435/96 |
| 5,334,516 | 8/1994 | Muramatsu et al. | 435/101 |

FOREIGN PATENT DOCUMENTS

| | | | |
|---|---|---|---|
| 0307158 | 3/1989 | European Pat. Off. | C08B 37/00 |
| 59-095895 | 6/1984 | Japan . | |

OTHER PUBLICATIONS

Hirayama et al., *Stud. Plant Sci.*, vol. 3 (Inulin and Inulin-Containing Crops), pp. 347–353. (1993) Abstract Only.
Schlubach et al, Leibigs Ann. Chem., 614 (1958): 119–123.
Schlubach et al, Liebigs Ann. Chem., 614 (1958): 126–136.
Schlubach et al, Liebigs Ann. Chem., 635 (1960):154–165.
Schlubach et al, Liebigs Ann. Chem., 578 (1952):194–198.
Bancal et al, Carbohydrate Research, 217 (1991):137–151.

*Primary Examiner*—John Kight
*Assistant Examiner*—Howard C. Lee
*Attorney, Agent, or Firm*—Hayes, Soloway, Hennessey, Grossman & Hage, P.C.

[57] ABSTRACT

Branched fructo-oligosaccharides consisting of a chain which comprises mainly fructose units and has a preferred chain length of 2 to 15 units, on which are fixed one or more side chains mainly composed of fructose units. The length of the side chain, which may be straight or branched, is of 1 to 10 units. A composition consisting of one or more of the above mentioned branched fructo-oligosaccharides and, particularly, mixtures comprising, apart from the branched fructo-oligosaccharides, other ingredients such as proteins, lipids or fatty acids, carbohydrates, fibers and other additives, are also described.

14 Claims, 1 Drawing Sheet t = 0h t = 18h

BRANCHED FRUCTO-OLIGOSACCHARIDES, METHOD FOR OBTAINING THEM AND USE OF PRODUCTS CONTAINING THEM

This a continuation of application Ser. No. 07/920,472, filed as PCT/BE91/00014 Feb. 22, 1991, published as WO91/13076 Sep. 5, 1991, now abandoned.

SUBJECT OF THE INVENTION

The present invention relates to branched fructo-oligosaccharides which particularly exhibit sweetening and bulking agent properties.

It also relates to the products which contain these branched fructo-oligosaccharides and to their use.

Finally, the present invention applies to the particular processes for their preparation.

SUMMARY OF THE PRIOR ART

A sedentary lifestyle where physical labor has nearly disappeared has considerably changed food requirements.

As a general rule, too much is eaten and often in an unbalanced manner. Too much fat, too much salt, too few so-called slow (complex) sugars and too little fiber.

In particular, the proportion of so-called slow sugars in our diets has fallen considerably, thus limiting their energy contribution.

Currently, the so-called rapid sugars and fats supply the principal energy contributions in our diet. It has been known for a long time that an unbalanced diet leads in the long term to serious deficiencies or even to diseases, for example cardiovascular diseases.

Additionally, a diet which is poor in fibers seems to be the cause of many digestive system disorders.

There is increasing awareness of the close connection which exists between the general state of health and the eating habit. There is also a tendency to adapt the diet or more particularly the dietetics to individual needs.

Inter alia, the development and the use of sweeteners with a high sweetening power have allowed the consumer to better adapt his diet to his needs. These sweeteners make it possible to give a sweet taste to the foods which contain them without having to have recourse to high-calorie sugars.

In this way, beverages with a negligible calorie contribution have, for example, appeared on the market.

On the other hand, the use of bulking agents is often essential in a range of foods such as pastry, confectionery, etc.

Sucrose, or glucose or fructose syrups are usually used as bulking agents. Nevertheless, these sugars are highly calorific.

Again, "sugar substitutes" have appeared on the market which are characterized by a lower calorific contribution.

More particularly, the ideal bulking agent would be a low- or noncalorific natural product, which is safe to use, wholesome, well tolerated by the body, without any particular taste and which can be used in a similar way to sucrose.

The bulking agents meeting these requirements have a high commercial potential.

The bulking agents are low-calorie if they satisfy one of the two following conditions:
 of being only partially or not at all absorbed into the blood via the small intestine;
 of being absorbed into the blood via the small intestine but not metabolized or only slightly metabolized by the body.

The use of linear fructo-oligosaccharides as bulking agents is known. These sugars, whose natural presence in food has been known for a long time, can be obtained enzymatically (see Albon et al., J. Chem. Soc. (1953), p. 24–27; Kawai et al., Agr. Biol. Chem. Vol. 37, No. 9 (1973, p. 2111–2119; Tomoda et al., Kyoritsu Yakka Daigaku Nempo vol. 20 (1975) p. 1–8) or by hydrolysis of inulin.

The linear fructo-oligosaccharides can be produced industrially from sugar as described in the document GB-A-2000144 by obtaining products of GFn type (G=Glucose, F=Fructose, n=2 to 5, bonds of the type B (1–2), or by hydrolysis of inulin, producing a mixture of GFn and Fn (n=2 to 10 and more).

These fructo-oligosaccharides have the following advantageous properties: neutral and sweet taste, absence of smell, low calorific value, dietary fiber effect, bifidogenic effect and natural and nontoxic character. Furthermore, these products have technological characteristics such that they can be used according to the standard methods for preparation of sugars and syrups.

Likewise, they can be used as sugar substitute in standard applications, for example as sweeteners in foods and beverages or as base materials or excipients for the preparation of pharmaceutical products.

Furthermore, they can be used in any industrial application envisaged for sugars and syrups, such as the production of adhesives, humidifiers, insecticides, colorants, tanning agents, electrical insulators, binders for foundry cores or, in a more general way, as softeners and/or thickeners and, of course, more particularly in the dietary field as a product of low calorific value or as a product with a dietary fiber effect or with a bifidogenic effect.

As a general rule, the low-calorie bulking agents are only partially absorbed in the small intestine and, for this reason, pass into the large intestine where they undergo, partially or totally, a fermentation due to the intestinal flora.

This is a natural process which all fibers undergo and which is the cause of the beneficial effect arising from the fibers.

The bulking agent is converted by fermentation in the large intestine into a range of reaction products of which the principal ones are volatile fatty acids (VFA) and gases such as $CO_2$, $H_2$ and, in certain cases, $CH_4$.

These gases are principally removed by the blood and the lungs or, in part, by flatulence.

During the passage of the bulking agent through the small intestine, the molecules of the latter absorb water and pass into the large intestine. This can cause osmotic diarrheas when the bulking agent is taken in large quantities. Of course, this effect depends essentially on the water-absorbing power of the bulking agent and is, in general, higher in the case of substances based essentially on monosaccharides than in the case of saccharides with a higher degree of polymerization.

In particular, the linear fructo-oligosaccharides which are not absorbed or only slightly absorbed in the stomach and the small intestine are found almost entirely in the large intestine and, as a result of their oligosaccharide nature (low degree of polymerization), they cause osmotic diarrheas only when they are taken in large quantities.

However, when they are ingested in large quantities, the linear fructo-oligosaccharides can give rise to a variety of unpleasant consequences (and of disorders) due principally to their fermentable character: increased flatulence, intestinal cramps, gastric noises, soft stools or even diarrheas.

More precisely, traces of linear fructo-oligosaccharides are not found in stools, even when large quantities have been ingested: this shows that they have undergone complete fermentation by the intestinal flora.

In fact, it has been proved that the linear fructo-oligosaccharides are degraded by bacteria belonging to the Bifidobacterium family, which shows the bifidogenic character of the linear fructo-oligosaccharides.

It is well understood that these various phenomena depend on the dose ingested, the sensitivity of the person concerned, the form in which the product containing the fructo-oligosaccharides is given, the time span over which the amounts were ingested, possibly the period of adaptation to the product and the composition of the other ingredients and, finally, the nature of the bulking agent ingested.

Moreover, these are disorders which have been known for a long time, in particular during the ingestion of large quantities of plums, cherries or onions.

These undesirable side effects are the cause of the fact that the use of these low-calorie bulking agents is not unlimited.

In particular, for certain agents, legislation has established a maximum daily dose. This dose amounts, for example, to 30 g for certain sugar alcohols (poly-alcohols derived from sugar).

Even in the case of bulking agents consisting of linear fructo-oligosaccharides, these disadvantages persist although the latter are in general better tolerated by the body, probably due to the fact that the osmotic effect is less than for certain sugar alcohols.

More particularly, it has become apparent that the long chain fructo-saccharides, such as inulin, cause osmotic phenomena which are less marked still. However, the negative effects due to fermentation by the intestinal flora have not completely disappeared.

Furthermore, these fructo-oligosaccharides exhibit a solubility which decreases and a viscosity which increases as the chain length increases.

The result of this is that the long chain fructo-saccharides do not exhibit all the appropriate technological properties for use as bulking agents instead and in place of sugar.

Moreover, fructose polymers have already been described in the following documents:

In Indian Journal of Biochemistry & Biophysics, vol. 13, Dec. 1976, pp. 398–419, Satyanarayana describes branched oligosaccharides which may be found in small quantities in nature. It seems that fructosyltransferase which is isolated from the Vera Cruz agave is unable to synthesize this branched oligosaccharide; it is thus not possible to obtain it in large quantities.

Likewise, in Liebigs Annalen der Chemie, 614, 126 (1958), Schlubach described branched oligosaccharides which can be found in small quantities in nature.

In Liebigs Annalen der Chemie, 635, 154 (1959), Schlubach also described natural products consisting of polymerized and branched fructose units which cannot be obtained naturally in large quantities.

In Agric. Biol. Chem., 52(4) 1303–1304 (1988), Muramatsu describes how oligosaccharides whose structure is identical to the products described in the patent EP-0307158 are obtained from sucrose via a microorganism.

In Carbohydrate Research, 180 (1988), 315–324, Brasch et al. described a fructose polymer (average chain length: 18) where 15% of the fructose units contain a branching point at the 0→6 position. Nevertheless, as a result of their excessively great chain length, these molecules do not constitute a suitable bulking agent.

The patent EP-0,307,158 of Nihon Shokuhin describes a fructose polymer where a branching point appears on a glucose unit.

The document J. of Chem. Soc., p. 1822–1830 (1951) describes a branched polyfructose, wherein the number of fructose units are estimated between 18 and 30 units.

The document Liebigs annalen der Chemie, 647, 41 (1961) describes fructo-oligosaccharides which present either a single branch upon the glucose unit (the neokestose or the neobifurcose series), or a single branch upon a fructose unit (the kestose, the bifurcose or the phlein derivatives of the bifurcose).

The document New Zealand J. of Thechnologie, vol. 1, No. 1, p. 27–31 (1985) describes a branched fructo-oligosaccharide extracted from "cordyline australis" with an average chain length of 18 units.

The patent application GB-2 105 338 describes an enzymatic treatment process allowing the obtention of a non-branched oligosaccharide constituted of one to four fructose molecules linked to a sucrose molecule.

AIMS OF THE INVENTION

The present invention aims to produce bulking agents which do not exhibit or which exhibit in a greatly abated way, the undesirable digestive disorders due to the conventional bulking agents.

Another aim of the present invention is to supply a bulking agent which exhibits the same advantageous properties as the linear fructo-oligosaccharides, such as neutral and sweet tastes, absence of smell, low calorific value, dietary fiber effect, bifidogenic effect and natural and non-toxic character of the product.

Another aim of the present invention consist in producing products which are soluble.

Another aim of the present invention consist in supplying products which can be used in a conventional way, using the standard processes for preparing sugars and syrups.

Other complementary aims of the present invention ie in the use of the product of the invention as a sweetener, as a low-calorie or weakly cariogenic food, as bifidogenic product or a product with a fiber effect, as a means of lowering the cholesterol level or of improving the condition of the intestinal flora, etc.

Other aims and advantages will become apparent in the description which follows.

DESCRIPTION OF THE INVENTION

The present invention relates to branched fructo-oligosaccharides according to claims 1 to 6.

The present invention also relates to a composition consisting of one or more branched fructo-oligosaccharides according to the invention and, more particularly, to mixtures consisting, in addition to the branched fructo-oligosaccharide(s), of other ingredients such as proteins, lipids or fatty acids, carbohydrates, fibers and other additives.

In particular, these ingredients may be products taken from the following nonlimiting list: sweeteners such as saccharose, products of the hydrolysis of the starch, palatinose, sucrose, glucose, fructose, glucose syrups or polyalcohols derived from sugar such as sorbitol, xylitol, erythritol, mannitol, maltitol, lactitol or isomalt, leucritol;

bulking agents such as polydextrose, cellulose, hemicellulose or fructo-oligosaccharides; or, again, sweeteners with a high sweetening power such as aspartame, acesulfame, saccharin, stevioside, sucralose and other dipeptide sweeteners, etc.

The products according to the invention are particularly suitable for use in human or animal feeding as bulking agents, as sweeteners, as low-calorie or weakly cariogenic foods, as bifidogenic products or products which improve the intestinal flora, as products with a dietary fiber effect, as agents for reducing the cholesterol level or, again, to improve the tolerance of food products. The present invention relates also to a pharmaceutical composition comprising a branched fructo-oligosaccharide according to the invention and possibly a suitable carrier.

Finally, the present invention also relates to processes for preparing these branched fructo-oligosaccharides.

In particular, the products according to the invention can be obtained by synthesis from sugar or from mixtures of fructose, optionally through the intermediacy catalysts or enzymes or by interaction of various enzymes with the sucrose of the fructo-oligosaccharides, inulin or fructans or chemically, that is to say by polymerization, principally of fructose, or by extraction from vegetable sources containing the said fructans, or, again, by hydrolysis of branched fructose polymers.

The fructo-oligosaccharides according to the invention can, in particular, be obtained from sucrose, fructose syrups, fructose in the crystalline form, fructans, levans, inulin, their hydrolysis products or, finally, products extracted from plants containing fructans.

Through the intervention of various enzymes, such as for example fructosyltransferase, levansucrase, etc., it is also possible selectively to form bonds which make it possible to implant fructose units at specified positions on other fructose units in the oligosaccharide chains. Enzymes may be used either consecutively or simultaneously. Preferably, enzymes will be used which preferentially form different bonds from those of the substrate.

For the production of branched fructo-oligosaccharides, optionally enzymatic processes of condensation or of synthesis, or, again, hydrolytic processes may be used.

By condensation of fructose monomers, it is possible to obtain an "at random" polymerization which may be followed by a chromatographic separation.

It is also possible to obtain branched fructo-oligosaccharides by hydrolysis of synthesized branched molecules or of those which exist in the natural state.

In this case, it is also possible to use several different hydrolysis techniques, especially the technique of acid hydrolysis, the technique of alkaline hydrolysis or the technique of enzymatic hydrolysis.

In particular, specific enzymatic hydrolysis such as, for example, the interaction of endoinulase with the mixture of branched fructans isolated from Cordyline australis ("cabbage tree"), which specifically attacks the $\beta(2\to1)$ bonds, gives rise to branched fructo-oligosaccharides.

The result depends on the nature of the starting material and on the hydrolysis technique used and, optionally, the enzymes used for the hydrolysis process and the reaction conditions. According to the reaction conditions, new branching points may be produced during the hydrolysis reaction of branched or linear molecules.

Reducing end groups can, in addition, be chemically converted, for example by oxidation, by reduction or by hydrogenation, etc.

The present invention also relates to a process which makes it possible to render the inulin more soluble by a very incomplete hydrolysis, followed by a branching reaction.

Figure 1A:
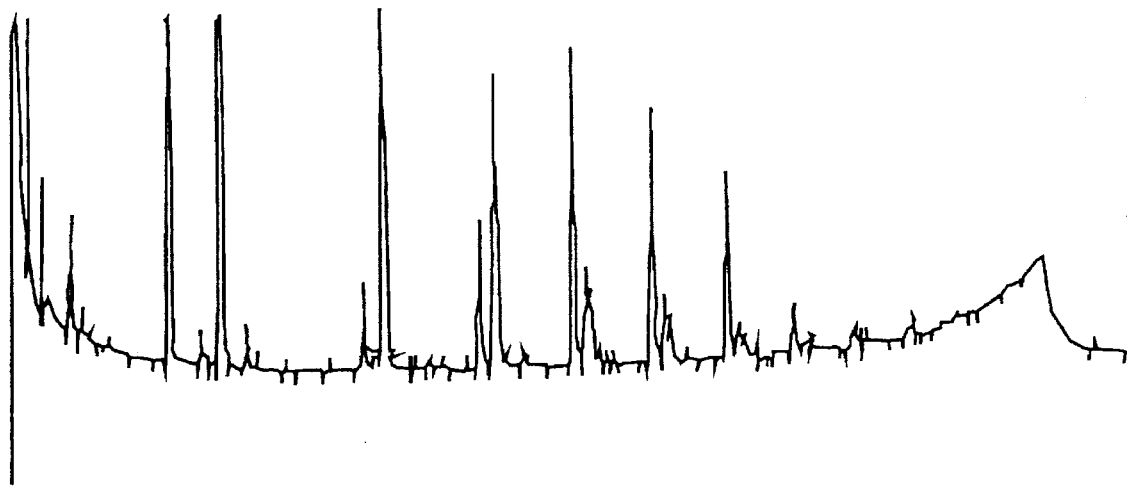
FIG. 1—A chromatogram of the fructo-oligosaccharide mixture of Example 2 before and after hydrolysis.

The processes used and the products obtained are better described with the help of the examples which follow.

EXAMPLE 1

Preparation of branched fructan polymers by hydrolysis

A mixture of branched fructans can be obtained from the "cabbage tree" (Cordyline australis) by extracting with methanol, washing with water followed by precipitation in an acetone/ethanol solution and drying.

The substances obtained consist principally of glucose and fructose units in a ratio of 1 to 16, arranged in chains with an average degree of polymerization equal to 18, where approximately 15% of the fructose units have a branching point.

A 25° Brix solution is heated to 90° C. and then 2N HCl is rapidly added until a pH of 2.5 is obtained. After reacting for 2 minutes, the hydrolysis is stopped by adding NaOH (3M) until a pH of 6.5 is obtained.

This solution is then filtered and demineralized by a double treatment on cationic and anionic ion exchangers. The glucose, the fructose and the sucrose formed by hydrolysis are then removed by chromatographic separation on a cationic column in the potassium form. The mixture of oligosaccharides thus obtained contains between 5 and 10% of mono- and disaccharides and from 90 to 95% of oligosaccharides. The average degree of polymerization of the composition thus obtained is approximately 5 and approximately 40% of the molecules therein are branched.

EXAMPLE 2

Preparation of the product according to the invention by synthesis

In this case, the enzyme levansucrase, derived from Bacillus subtilis, is used.

It has been observed that this enzyme, when incubated under suitable conditions in the presence of sucrose and of fructo-oligosaccharides of the $\beta(2\to1)$ type, forms branched fructo-oligosaccharides.

In this example, the base fructo-oligosaccharides used are obtained by enzymatic hydrolysis of inulin by endo-inulinase obtained from the enzymatic preparation Novozyme 230.

A 40° Brix solution consisting of 50% sucrose and 50% base fructo-oligosaccharides is prepared in a 0.05M phosphate buffer solution at a pH of 6.

A solution of levansucrase which contains 20 U/ml —1 U being the quantity of enzyme necessary to release 1 micromole of glucose per minute—is added to the mixture in such a way as to obtain 4 U of levansucrase per gram of dry carbohydrate matter in the mixture. The solution is then incubated at 30° C. for 18 hours in an orbital shaker (150 rev/min). The enzymatic reaction is then halted by cooking the reaction mixture for 5 minutes. Linear, long chain $\beta$-fructans (DP>12) are separated off by precipitating with 80% ethanol.

After centrifuging (30 minutes at 5000 rev/min) and evaporating off the ethanol under vacuum, the solution is demineralized on ion exchangers such as described in Example 1.

Figure 1B:
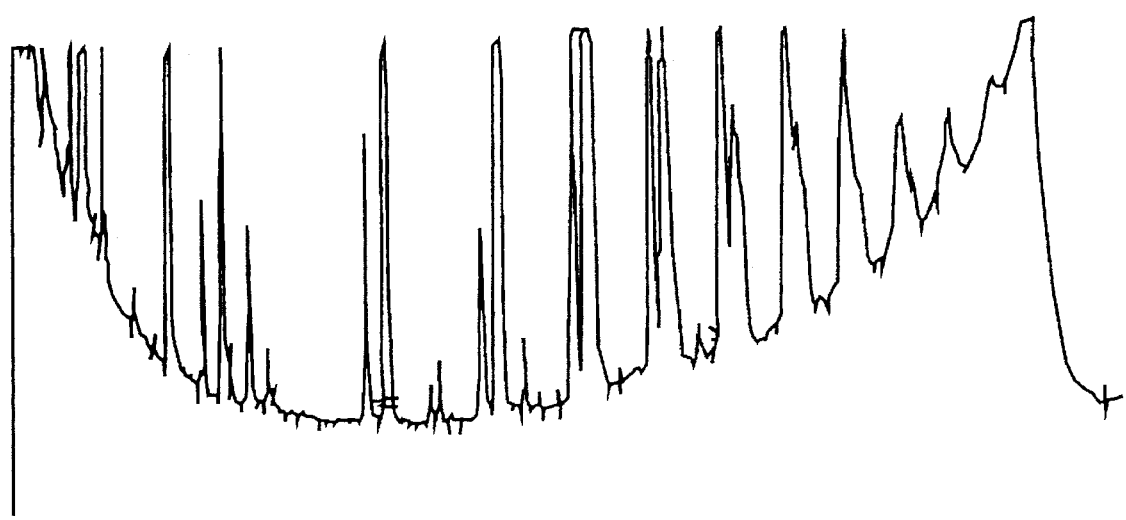

The mixture obtained is then subjected to a chromatographic analysis. The chromatogram is represented in FIG. 1.

The reaction mixture contains at this point approximately 27% glucose, 3% fructose, 3% sucrose and 67% fructans with a DP>2, of which approximately 60% has a DP<12 and 40% has a DP≧12. This fraction with a DP≧12 cannot be precipitated with 80% ethanol, which is an indication of its branched nature. Approximately 40% of the molecules which have a DP of 3 to 12 are branched (cf. chromatogram FIG. 1).

The monosaccharides are principally removed by chromatographic separation.

The final product thus obtained contains approximately 90 to 95% of oligosaccharides with an average degree of polymerization equal to 4.5–5 and where 40 to 50% of the molecules are branched.

The branched fructo-oligosaccharides exhibit unexpected tolerance properties while still retaining the other advantageous properties of linear fructo-oligosaccharides: neutral and sweet taste, absence of smell, low calorific value, dietary fiber effect, bifidogenic effect and natural and nontoxic character.

The branched fructo-oligosaccharides can also be used as sugar substitutes in all the standard and industrial applications described for linear fructo-oligosaccharides.

The improved tolerance of these branched fructo-oligoposaccharides was demonstrated by carrying out the following in-vitro and in-vivo tests:

1. IN-VITRO Tests

Fresh fecal materials from male subjects in good health were homogenized with 5 times their weight of isotonic NaKCl in an anaerobic environment. Five 10 ml aliquot fractions of this homogenized mixture were used per test group.

As reference test group, 5 incubations were carried out in test tubes containing 20 g/l of a mixture of fructo-oligosaccharides consisting of 5% of glucose, fructose and sucrose, 35% of GF2, 50% of GF3 and 10% of GF4 (G=glucose, F=fructose).

As second test group, 5 incubations were carried out in test tubes containing 20 ml/l of the mixture of branched fructo-oligosaccharides described in Example 1.

The test tubes are sealed with a sheet of paraffin wax whose displacement indicates the production of gas.

The formation of gas was monitored for 12 hours. It is expressed in centimeters of displacement per hour.

These tests show that the formation of gas per hour in the case of branched fructo-oligosaccharides reaches only 35% of that due to linear fructo-oligosaccharides.

2. IN-VIVO Tests

During an experiment carried out on three male subjects sensitive to fermentation in the large intestine, various quantities of fructo-oligosaccharides were mixed in fruit juices taken at breakfast, this breakfast usually consisting of fruit juice, bread and coffee in the usual quantities. The dose introduced is gradually increased in 10 g doses from an initial dose also of 10 g. Between two test breakfasts, at least two days elapse without any test.

The reactions of the subjects were recorded for each concentration and more specifically as regards the following criteria: flatulence, gastric noises, intestinal cramps, soft stools and diarrhea. The "stopping dose" is defined as the first dose where one or more of these side effects are felt to be uncomfortable.

The substances tested which were introduced into the fruit juice are the following:

substance A: mixture of linear fructo-oligosaccharides such as described above in the prior art;
substance B: mixture of branched fructo-oligosaccharides such as described in Example 2.
substance C: mixture containing 50% of substance A and 50% of substance B.

The results obtained are described in the following table:

| STOPPING DOSE | A | B | C |
| --- | --- | --- | --- |
| VOLUNTEER 1 | 20 g | 40 g | 30 g |
| VOLUNTEER 2 | 30 g | 60 g | 50 g |
| VOLUNTEER 3 | 40 g | 60 g | 50 g |

From this table, it can be concluded that the branched fructo-oligosaccharides are tolerated better than the linear oligosaccharides and that by introducing a certain quantity of branched fructo-oligosaccharides into a mixture which also comprises linear fructo-oligosaccharides, the tolerance of this mixture is increased.

Properties

Low-calorie product

The branched fructo-oligosaccharides are not hydrolyzed by human digestive enzymes. These substances thus have a low calorie contribution.

Weakly cariogenic product

The branched fructo-oligosaccharides are less cariogenic than sucrose. This is explained by the fact that they are not used as substrate for the formation of dental plaque and that they are less capable of causing the formation of acid by the oral flora.

Products with bifidogenic activity and which improve the intestinal flora

The branched fructo-oligosaccharides have a selective bifidogenic effect: they stimulate in a specific way the growth of the bifid population in the large intestine. This is explained by the fact that these fructo-oligosaccharides are used as an energy source by the bacteria belonging to the Bifidobacteria group, whereas other bacteria are much less able to use this substrate. In particular, a certain number of putref-active bacteria (such as Salmonella and Clostridium) have their growth limited, which brings about a qualitative and quantitative improvement in the intestinal flora.

Product with dietary fiber effect and which reduces the cholesterol level

The fructo-oligosaccharides have a dietary fiber effect: they reduce the intestinal transit time and increase the fecal mass. This is explained by the fact that these fructo-oligosaccharides are not absorbed in the small intestine and pass into the large intestine where they undergo a fermentation. These fructo-oligosaccharides also cause a reduction in the blood cholesterol level as a result of their dietary fiber effect.

Diuretic agent

The branched fructo-oligosaccharides can be used for the prevention or the treatment of all those disorders which may be caused by the presence of products such as, for example, accumulated degradation products which can be the cause of kidney disorders, liver disorders or of cancer, etc.

Product which improves the tolerance of other products

It is already known that branched fructo-oligosaccharides are tolerated better than their linear analogs.

Indeed, the branched molecules constitute fermentation substrates which are more difficult for the intestinal flora; the fermentation is thus retarded by the presence of these molecules.

It is thus possible to improve the tolerance of fermentable foods by adding branched fructo-oligosaccharies to the diet, due to the reduction and slowing-down of the fermentation phenomena.

Solubility of the product

The branched fructo-oligosaccharides have a higher solubility than that of the linear compounds, which allows them to be used more readily in a certain number of products (cold sparkling or dairy drinks, other dairy products, confectionery, biscuits, etc.) where high concentrations of sugars must be used.

The combination of these last two properties, namely the increased tolerance of the branched fructo-oligosaccharides and the increased solubility of the product according to the invention favor their use as bulking agents.

Increased stability in acids medium

The branched fructo-oligosaccharides have better stability in acidic medium than the linear compounds, and this makes it possible to limit their degradation (formation of saccharides such as fructose, glucose and sucrose) during the manufacture and the storage of acidic foods and to guarantee that the latter have characteristics which are more constant during their lifetime.

The increase in the stability in acidic medium was revealed during a comparative experiment carried out with two substances:

Substance A: mixture of linear fructo-oligosaccharides containing
   5% of glucose, fructose and sucrose
   35% of GF2
   50% of GF3
   10% of GF4

Substance B: mixture of branched fructo-oligosaccharides as described in Example 1.

Each of the substances A and B was taken up in 10° Brix aqueous solution; the pH was then adjusted to 3.5 with the aid of hydrochloric acid.

The solutions thus obtained were stored for several weeks at 20° C. The stability of the fructo-oligosaccharides in these solutions was followed by the development of glucose and sucrose contents (determined by gas chromatography) during storage.

The results obtained are described in the table below:

TABLE

| Storage time | Fructose, glucose and sucrose content in % | |
|---|---|---|
| | Substance | |
| at 20° C. and pH = 3.5 | A | B |
| 0 | 5 | 5 |
| 4 weeks | 18 | 11 |
| 8 weeks | 32 | 21 |

Applications

The branched fructo-oligosaccharides can be incorporated into foods or prepared in the form of granules or tablets. In the latter case, they can be used as oral pharmaceutical compositions, for example to selectively stimulate the growth of the bifid population, as a diuretic, etc.

The fructo-oligosaccharides have properties comparable to those of sugar and glucose syrups; they can therefore be used in the same way. They can replace sugar and glucose syrups in the majority of applications, especially in the following products:

confectionery (sweets, etc.), jelly products (gums, etc.), chocolate-based preparations, chewing gum, biscuits, ice creams and sorbets, dairy products, fruit-based drinks, fruit jams and preparations, caramels, pharmaceutical preparations, etc.

The branched fructo-oligosaccharides have, in particular, suitable properties for replacing sugar and glucose syrups in the preparation of low calorie, weakly cariogenic, bifidogenic and/or diet products.

The present invention is illustrated by a non-limiting range of examples of possible applications.

As base product, a syrup of branched fructo-oligosaccharides, prepared as described in Example 1 or Example 2, was used.

The products according to the invention were evaluated by a panel of about twenty tasters in order to compare their properties with those of conventional products based on sucrose and/or glucose syrup. These tests revealed a high acceptance of products based on branched fructo-oligosaccharides.

EXAMPLE 3

Preparation of a milk ice cream

| Ingredients (by weight): | |
|---|---|
| Skimmed milk powder | 13.00 |
| Water | 62.46 |
| Cream (35% fatty matter) | 8.60 |
| Branched fructo-oligosaccharides of Example 1 | 15.00 |
| Stabilizer (Cremodan SE30, Grindsted Products) | 0.50 |
| Vanilla flavoring agent (Silesia 111/8309280) | 0.40 |
| Aspartame (NutraSweet) | 0.04 |
| Composition: | |
| Total solids | 28.5% |
| Milk solids | 16.0% |
| Milk fats | 3.0% |

Preparation:

The various ingredients in powder form are mixed while dry and dissolved in water.

The branched fructo-oligosaccharides, the flavoring agent and the cream are then added. The whole is mixed until a homogeneous product is obtained. The mixture is heated to 80° C. and this temperature is maintained for 30 seconds. The mixture is then homogenized while hot (mixer), cooled to 5° C. and left to stand for a few hours in the refrigerator. It is aerated (100%) and frozen in an ice cream making machine (Carpigiani).

It is stored in a deep freeze.

EXAMPLE 4

Preparation of a sorbet

| Ingredients (by weight): | |
|---|---|
| Strawberry purée (6.5% solids) | 74.48 |
| Branched fructo-oligosaccharides of Example 1 | 25.00 |
| Stabilizer (Fructodan SL64, Grinsted Products) | 0.45 |
| Aspartame (NutraSweet) | 0.07 |

Composition: 25% solids.

Preparation:

The ingredients are thoroughly mixed, heated to 80° C. and held at this temperature for 30 seconds. The mixture is then cooled to 5° C. and kept in the refrigerator for a few hours. It is aerated (75%) and frozen in an ice cream making machine (Carpigiani)

It is stored in a deep freeze.

EXAMPLE 5

Preparation of a jam

| Ingredients (by weight): | |
| --- | --- |
| Strawberries (10% solids) | 65.00 |
| Branched fructo-oligosaccharides of Example 1 | 42.00 |
| Water | 25.00 |
| Pectin (LM 27NH95, Sanofi Bio-Industrie) | 1.00 |
| Citric acid (50%) | 0.80 |

Composition: 40% solids.

Preparation:

The pectin is dissolved in warm water (60° C.), and it is then thoroughly mixed with the strawberries. The mixture is left to cook, with thorough stirring, until a product with a weight of 57 g is obtained.

The branched fructo-oligosaccharides, heated to 60° C., are then added. The citric acid is then added. The mixture is allowed to cool to 75° C. and is packed into glass jars.

EXAMPLE 6

Preparation of a yoghurt

| Ingredients (by weight) | |
| --- | --- |
| Whole milk (3.7% fatty matter) | 94.10 |
| Skimmed milk powder | 1.90 |
| Yoghurt fermenting agents | 1.00 |
| Branched fructo-oligosaccharides of Example 1 | 3.00 |
| Composition: | |
| Total solids | 16.0% |
| Milk solids | 13.5% |
| Milk fats | 3.5% |

Preparation:

The milk powder and the branched fructo-oligosaccharides are mixed with the cold milk. The mixture is then heated to 60° C. and homogenized. It is then heated to 90° C. and held at this temperature for 10 minutes.

The mixture is cooled to 45° C. and is seeded with lactic fermenting agents. The mixture is transferred into preheated pots and incubated at 43° C. to a pH of 4.2.

The product is stored at 10° C. maximum.

EXAMPLE 7

Preparation of a fruit cake

| Ingredients (by weight) | |
| --- | --- |
| Branched fructo-oligosaccharides of Example 1 | 25.30 |
| Margarine | 8.50 |
| Whole eggs | 10.10 |
| Ammonium carbonate/bicarbonate | 0.40 |
| Flour | 33.65 |
| Milk | 6.80 |

-continued

| | |
| --- | --- |
| Raisins | 10.10 |
| Dried fruit | 5.10 |
| Acesulfame K | 0.05 |

Preparation:

Mix the branched fructo-oligosaccharides with the margarine, add the eggs, and the ammonium carbonate, the Acesulfame K and the bicarbonate dissolved in 0.5 liter of milk. Add the flour and the rest of the milk. Mix until a homogeneous mixture is obtained. Then add the raisins and the dried fruit. Transfer the whole into a mold and bake in an oven at 250° C.

EXAMPLE 8

Preparation of a sponge cake

| Ingredients (by weight): | |
| --- | --- |
| Branched fructo-oligosaccharides of Example 1 | 27.00 |
| Eggs | 49.80 |
| Flour | 27.00 |
| Butter | 8.30 |
| Acesulfame K (Hoechst) | 0.05 |

Preparation:

Beat the branched fructo-oligosaccharides and the whole eggs in a bain-marie until a thick foam is obtained which has a density of ±0.75.

Sift the flour and add it to the paste while mixing gently. Heat the butter until it is half melted and mix it with the dough. Pour the dough into a pregreased mold and cook in the oven for 20 minutes at 175°.

EXAMPLE 9

Preparation of gums

| Ingredients (by weight): | |
| --- | --- |
| Branched fructo-oligosaccharides of Example 2 | 94.00 |
| Gelatin 200 BLS (Sanofi Bio-Industrie) | 6.50 |
| Water | 13.50 |
| 50% citric acid solution | 1.50 |
| Cola LE 1613 (Sanofi Bio-Industrie) | 0.10 |
| Aspartame | 0.26 |

Solids content of the finished product: 80%.

Preparation:

The gelatin is dissolved in hot water (80° to 90° C.). The branched fructo-oligosaccharides are cooked at 115° C. The syrup is then cooled to 100° C. The gelatin solution is then added to this syrup. The air bubbles are removed from this syrup by bringing it under vacuum or by leaving it to stand. The mass is cooled to approximately 80° C. The flavoring agent, the colorant, Aspartame and citric acid are added and the mixture is poured into starch molds. The starch is used at a temperature of approximately 30°–35° C. The gums are covered with a starch layer and are left to stand for 24 hours at room temperature. The powder is then removed from the gums and the latter are coated with oil.

EXAMPLE 10

Preparation of hard gums

| Ingredients (by weight): | |
| --- | --- |
| Branched fructo-oligosaccharides of Example 2 | 96.50 |
| Gelatin GAT 15 | 11.00 |
| Water | 16.50 |
| 50% citric acid solution | 1.50 |
| Mandarin flavoring agent LE 1450 (Sanofi Bio-Industries) | 0.25 |
| Aspartame | 0.28 |

Solids content of the finished product: 88%.
Preparation:

The gelatin is dissolved in hot water (80°–90° C.).

The branched fructo-oligosaccharides are cooked at 113° C. The syrup is then cooled to 100° C. The gelatin solution is then added to this syrup. The air bubbles are removed from this syrup and the mass is cooled to approximately 80° C. The flavoring agent, the colorant, Aspartame and citric acid are added. The mixture is poured into starch molds. The starch is used at a temperature of approximately 30°–35° C.

The gums are covered with a starch layer. They are left to stand in a ventilated oven for 72 hours at 50° C. The powder is then removed from the gums and the latter are coated with oil.

EXAMPLE 11

Preparation of hard sweets

| Ingredients (by weight): | |
| --- | --- |
| Branched fructo-oligosaccharides of Example 1 | 125.00 |
| Citric acid (100%) | 0.83 |
| Extract BE4017 (Sanofi Bio-Industrie) | 0.10 |
| Lemon flavoring agent LE 1616 (Sanofi Bio-Industrie) | 0.15 |
| Acesulfame K | 0.34 |

Solids content of the finished product: 98%.
Preparation:

The branched fructo-oligosaccharides are heated at a temperature of 165° C. until a solids content of 98% is obtained.

The syrup is cooled to a temperature of ±110° C.; the colorant, the flavoring agent, Acesulfame K and citric acid are then mixed with the product obtained. The product obtained is then poured into molds. After cooling, the sweets are removed from the molds.

EXAMPLE 12

Preparation of caramels

| Ingredients (by weight) | |
| --- | --- |
| Branched fructo-oligosaccharides of Example 1 | 68.60 |
| Sweetened condensed milk | 26.00 |
| Fat melting at 32° C. | 5.20 |
| Salt | 0.20 |
| Lecithin | 0.20 |
| Acesulfame K | 0.24 |

Preparation:

Dissolve the lecithin in the fat in a bain-marie at 70° C.

Pour the branched fructo-oligosaccharides, the sweetened condensed milk, the salt, Acesulfame K and the mixture consisting of fat and lecithin into a cooking pot. Mix and heat the mixture to 55°–60° C.

Raise the temperature to 119°–121° C. Then pour onto a cooling tray and allow to cool to 35°–40° C.

EXAMPLE 13

Preparation of a pudding

| Ingredients (by weight): | |
| --- | --- |
| Skimmed milk | 84.94 |
| Skimmed milk powder | 1.80 |
| Branched fructo-oligosaccharides of Example 1 | 10.00 |
| Aspartame (NutraSweet) | 0.03 |
| Starch (Snowflake 06304, Cerestar) | 3.00 |
| Carrageenan (Genulacta SGI-1, Hercules) | 0.20 |
| Vanilla flavoring agent (Flav-o-lok 630019H, PFW Products) | 0.02 |
| Cream-yellow colorant (51798, Ned. Kleurstofindustrie) | 0.01 |

Composition: 20% solids.
Preparation:

The ingredients in powder form are mixed while dry; the cold milk is then added. The ingredients are then mixed until a homogeneous mixture is obtained.

The mixture is heated to 95° C. and is held at this temperature for 5 minutes.

The whole is cooled to 50° C. while stirring the mixture. The mixture is packed into dishes and stored in the refrigerator.

EXAMPLE 14

Preparation of a fruit-based drink

| Ingredients (by weight): | |
| --- | --- |
| Concentrated fruit juice (Orange PG31332, Quest Int.) | 3.80 |
| Branched fructo-oligosaccharides of Example 1 | 7.00 |
| Sucrose | 7.50 |
| Citric acid (50%) | 0.30 |
| Water | 81.40 |
| Composition: | |
| Solids | 14.5% |
| Fruit juice | 15.0% |

Preparation:

Dissolve the sugar in the water. Add the other ingredients and mix thoroughly. Store in the refrigerator.

EXAMPLE 15

Enzymatic treatment of inulin

A 40 Brix solution, consisting of 50% sucrose and 50% inulin, which contains a large proportion of molecules with a high degree of polymerization (DP), is adjusted to a pH of 5.4. This solution is divided into two fractions.

A solution of levansucrase (LS) is added to the first fraction so as to obtain 2 U of levansucrase per gram of solid while bringing the pH to 5. The solution is then incubated at 37° C. for 18 hours. The enzymatic reaction is then halted by cooking the reaction mixture for five minutes. 0.6 U of endoinulase, obtained from the enzymatic preparation of Novozyme 230, per gram of solid is added to the second fraction. The incubation is halted after one hour by cooking the reaction mixture for five minutes. A solution of levansucrase is then added as described above. The percentage of precipitation in an 80% ethanol solution is determined for the various fractions:

|  | % of precipitate calculated for all the products with DP > 2 |
|---|---|
| Base solution | 66 |
| Base solution + LS | 40 |
| Base solution + endoinul. | 15 |
| Base solution + endoinul. + LS | 2.5 |

This shows that the action of levansucrase has a significant effect on the solubility of linear carbohydrates of the inulin type. It is evident that other linear chains, e.g. based on 2→6 (phlein type) bonds can also be branched by using a suitable enzyme, which preferentially forms other bonds than those of the linear chain such as, for example, of the 2→1 type (fructosyltransferase). This technique could even be applied to glucoside chains.

By starting from an inulin with a mean DP markedly lower than that used in the example, e.g. by starting from the inulin of Jerusalem artichoke, levansucrase can be made to act directly on the inulin without prior hydrolysis.

In tabular form, the gas phase chromatographic analysis of the various fractions. As can be seen from this table, an increase is recorded in the proportion of products with DP 5, DP 6, DP 7, DP 8, DP 9 and DP 10 and of soluble products which it was not possible to separate by means of the column used (DP 10+). In addition, it is possible to see on the chromatogram that the shape of certain peaks of the reaction product is different from the peaks of the starting material (the presence of a shoulder, showing the presence of two products) and that, in addition, other products have been formed which can no longer be found in the chromatogram of the levan. This clearly shows that levansucrase has transferred fructose molecules from the sucrose to the linear chain.

Glucose is then removed from the fraction which was treated with endoinulase and levansucrase by fermentation. The product thus obtained is permethylated by following the slightly modified method described in the paper by Goran Larson et al.: "Application of a simple methylation procedure for the analysis of glycosphingolipids", published in Carbohydrate Research, Vol. 161, p. 281–290 (1987).

After the permethylation, the hydrolysis which makes it possible to produce monosaccharides and the silylation of the monosaccharides, the latter are separated into dimethyl-, trimethyl- and tetramethylfructoses by gas phase chromatography. The presence of dimethylfructose in the chromatogram is proof of the presence in the saccharide chains of fructose molecules bonded to three other molecules. In addition, it is possible to detect isomers of trimethylfructose such as 3,4,6- and 1,3,4-trimethylfructose which indicates the presence in the molecules of 1→2 and 2→6 bonds. This clearly proves that the action of levansucrase on the linear chain of the inulin gives rise to branching points both of the type:

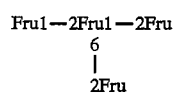

and of the type:

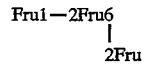

Table I which follows shows the result of the gas phase chromatographic analysis of the various fractions of the products of Example 15.

TABLE

|  | INULIN + SUCROSE (50/50) (A) | A + LS | A + ENDO 1 hr (B) | B + LS |
|---|---|---|---|---|
| Fructose | 1.3 | 4.8 | 1.4 | 3.6 |
| Glucose | 0.45 | 28 | 0.5 | 26.4 |
| Sucrose | 49.7 | 9.5 | 51.4 | 4.6 |
| DFA | 0.2 | 0.3 | 0.3 | 0.2 |
| F2 | 0.4 | 0.2 | 0.4 | 0.3 |
| GF2 | 1.3 | 0.6 | 1.3 | 0.8 |
| F3 | 1.6 | 0.01 | 6.5 | 2 |
| GF3 | 1.8 | 0.7 | 2 | 1 |
| F4 | 1.0 | 0.1 | 5.5 | 4.5 |
| GF4 | 2 | 0.9 | 4.3 | 1.6 |
| F5 | 0.4 | 2.4 | 3 | 4.9 |
| GF5 | 1.8 | 0.9 | 3.7 | 2.5 |
| F6 | 0.3 | 0.2 | 2 | 3.2 |
| GF6 | 1.4 | 1 | 3 | 2.9 |
| F7 | 0.1 | 0.1 | 1.2 | 2.7 |
| GF7 | 1.2 | 1.1 | 1.2 | 3 |
| F8 | 0.1 | 0.2 | 0.3 | 2.3 |
| GF8 | 1 | 1.3 | 0.6 | 2.8 |
| F9 | 0.05 | 0.1 | 0.2 |  |
| DP10 | 0.2 | 1.1 | 0 | 1.8 |
| DP10+ | 0 | 22 | 3.8 | 27 |
| Precipitate | 33 | 23.5 | 7.1 | 1.7 |

(DFA = Di-Fructose Anhydride)

We claim:

1. Composition comprising a branched fructo-oligosaccharide consisting of a main chain and of at least one side chain, which side chain comprises fructose units, the main chain contains from 2 to 15 fructose units and all the branching points are on fructose units and said branch comprises a fructose-fructose linkage said composition not including the following natural products: 1-kestose, 6-kestose, O-β-D-fructofuranosyl-(2→1)-O-β-D-fructofuranosyl-α-D-glucopyranoside, O-β-D-fructofuranosyl-(2→1)-β-D-fructofuranosyl-(2→1)-O-β-D-fructofuranosyl-α-D-glucopyranoside and the products having the following structure:

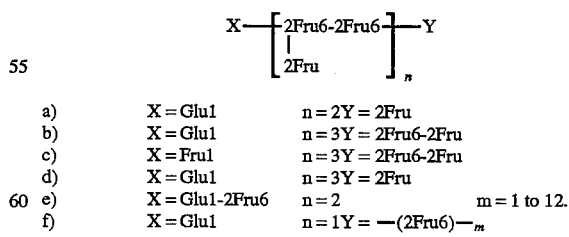

a) X = Glu1    n = 2 Y = 2Fru
b) X = Glu1    n = 3 Y = 2Fru6-2Fru
c) X = Fru1    n = 3 Y = 2Fru6-2Fru
d) X = Glu1    n = 3 Y = 2Fru
e) X = Glu1-2Fru6    n = 2    m = 1 to 12.
f) X = Glu1    n = 1 Y = —(2Fru6)—$_m$

2. Branched fructo-oligosaccharide according to claim 1, comprising at least one side chain which consists of 1 to 15 fructose units.

3. Branched fructo-oligosaccharide according to claim 1, comprising at least one side chain which is unbranched.

4. Branched fructo-oligosaccharide according to claim 1, comprising at least one side chain wherein said side chain is branched into additional side chains.

5. Composition comprising the branched fructo-oligosaccharide according to claim 1 as a component for use in a bulking agent, sweetener, low calorie agent, cariogenic agent, bifidogenic agent, intestinal flora agent, cholesterol reducing agent, dietary fiber or diuretic.

6. Composition according to claim 5, comprising at least one ingredient which is selected from the group consisting of a protein, lipid, fatty acid, carbohydrate, dietary fiber and an additive.

7. Composition according to claim 5, comprising at least one sweetener selected from the group consisting of sucrose, glucose, fructose, hydrolysis products of starch, palatinose, sorbitol, xylitol, erythritol, mannitol, maltitol, lactitol, isomalt, leucritol, polydextrose, cellulose, hemicellulose, a fructo- or other oligosaccharide and a sweetener with a high sweetening power.

8. A food product for consumption by human beings or animals comprising the branched fructo-oligosaccharide comprising the branched fructo-oligosaccharide according to claim 1 as a component in said food to be consumed by said human.

9. Pharmaceutical composition comprising the branched fructo-oligosaccharide according to claim 1 and a pharmaceutically acceptable carrier.

10. Pharmaceutical composition according to claim 9, further comprising a filler.

11. Composition comprising a 100% branched fructo-oligosaccharide consisting of a main chain having a polymerization degree higher than 8, and of at least one side chain, which side chain comprises fructose units, and all the branching points are on said fructose units and said branch comprises a fructose-fructose linkage said composition not including the following natural products: 1-kestose, 6-kestose, O-β-D-fructofuranosyl-(2→1)-O-β-D-fructofuranosyl-α-D-glucopyranoside, O-β-D-fructofuranosyl-(2→1)-β-D-fructofuranosyl-(2→1)-O-β-D-fructofuranosyl-α-D-glucopyranoside and the products having the following structure:

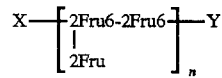

| | | |
|---|---|---|
| a) | X = Glu1 | n = 2 Y = 2Fru |
| b) | X = Glu1 | n = 3 Y = 2Fru6-2Fru |
| c) | X = Fru1 | n = 3 Y = 2Fru6-2Fru |
| d) | X = Glu1 | n = 3 Y = 2Fru |
| e) | X = Glu1-2Fru6 | n = 2  m = 1 to 12. |
| f) | X = Glu1 | n = 1 Y = —(2Fru6)—$_m$ |

12. Process for the preparation of branched fructo-oligosaccharides according to claim 1, wherein the process comprises supplying a branched fructan and partially hydrolizing said fructan to produced said branched fructo-oligosaccharides.

13. Process for the preparation of branched fructo-oligosaccharides according to claim 1 wherein the process comprises supplying a vegetable source containing branched fructans and extracting said branched fructans and partially hydrolizing the extract to obtain said branched fructo-oligosaccharides.

14. Process for the preparation of branched fructo-oligosaccharides comprising supplying a vegetable source containing branched fructans and extracting said branches fructans and hydrolyzing the extract to obtain said branched fructo-oligosaccharide wherein said branched comprises a fructose-fructose linkage.

* * * * *